United States Patent [19]

King et al.

[11] Patent Number: 5,127,410
[45] Date of Patent: Jul. 7, 1992

[54] ULTRASOUND PROBE AND LENS ASSEMBLY FOR USE THEREIN

[75] Inventors: Robert W. King, Lexington, Mass.; John W. Duffy, Sandown, N.H.; James N. C. Chen, Chelmsford, Mass.

[73] Assignee: Hewlett-Packard Company, Palo Alto, Calif.

[21] Appl. No.: 623,314

[22] Filed: Dec. 6, 1990

[51] Int. Cl.⁵ .................................. A61B 8/00
[52] U.S. Cl. .................. 128/662.03; 310/335; 310/336; 73/625
[58] Field of Search ............ 128/661.01, 662.03, 128/662.06; 310/335, 336; 73/625, 626

[56] References Cited

U.S. PATENT DOCUMENTS

| | | | |
|---|---|---|---|
| 3,387,604 | 2/1965 | Erikson | 310/369 |
| 3,958,559 | 5/1976 | Glenn et al. | 128/663.01 |
| 4,184,094 | 1/1980 | Kopel | 310/369 |
| 4,205,686 | 6/1980 | Harris et al. | 310/336 |
| 4,296,349 | 10/1981 | Nakanishi et al. | 310/335 |
| 4,385,255 | 5/1983 | Yamaguchi et al. | 310/335 |
| 4,387,720 | 6/1983 | Miller | 128/663.01 |
| 4,503,861 | 3/1985 | Entrekin | 128/662.04 |
| 4,718,421 | 1/1988 | Rohwedder et al. | 310/335 |
| 4,880,012 | 11/1989 | Sato | 128/663.01 |
| 4,901,729 | 2/1990 | Saitoh et al. | 128/662.03 |

Primary Examiner—Francis Jaworski
Assistant Examiner—George Manuel

[57] ABSTRACT

This invention provides an ultrasonic transducer probe for medical scanning and a lens assembly for use therein. The probe has a housing in which an ultrasonic transducer array is mounted, there being an opening in the housing adjacent the transducer array. A first lens subassembly is mounted to the transducer and moves therewith if the transducer is rotated. A second lens subassembly is mounted to the housing to fill the opening therein, and includes, for example, a thin plastic film covering the opening and bonded to the housing to seal the opening and a film backing lens or layer. The first lens subassembly is preferably a compound lens. The lens subassemblies are formed of materials having relative acoustic properties, and having mating surfaces which are shaped, to selectively focus ultrasonic signals from the transducers.

20 Claims, 1 Drawing Sheet

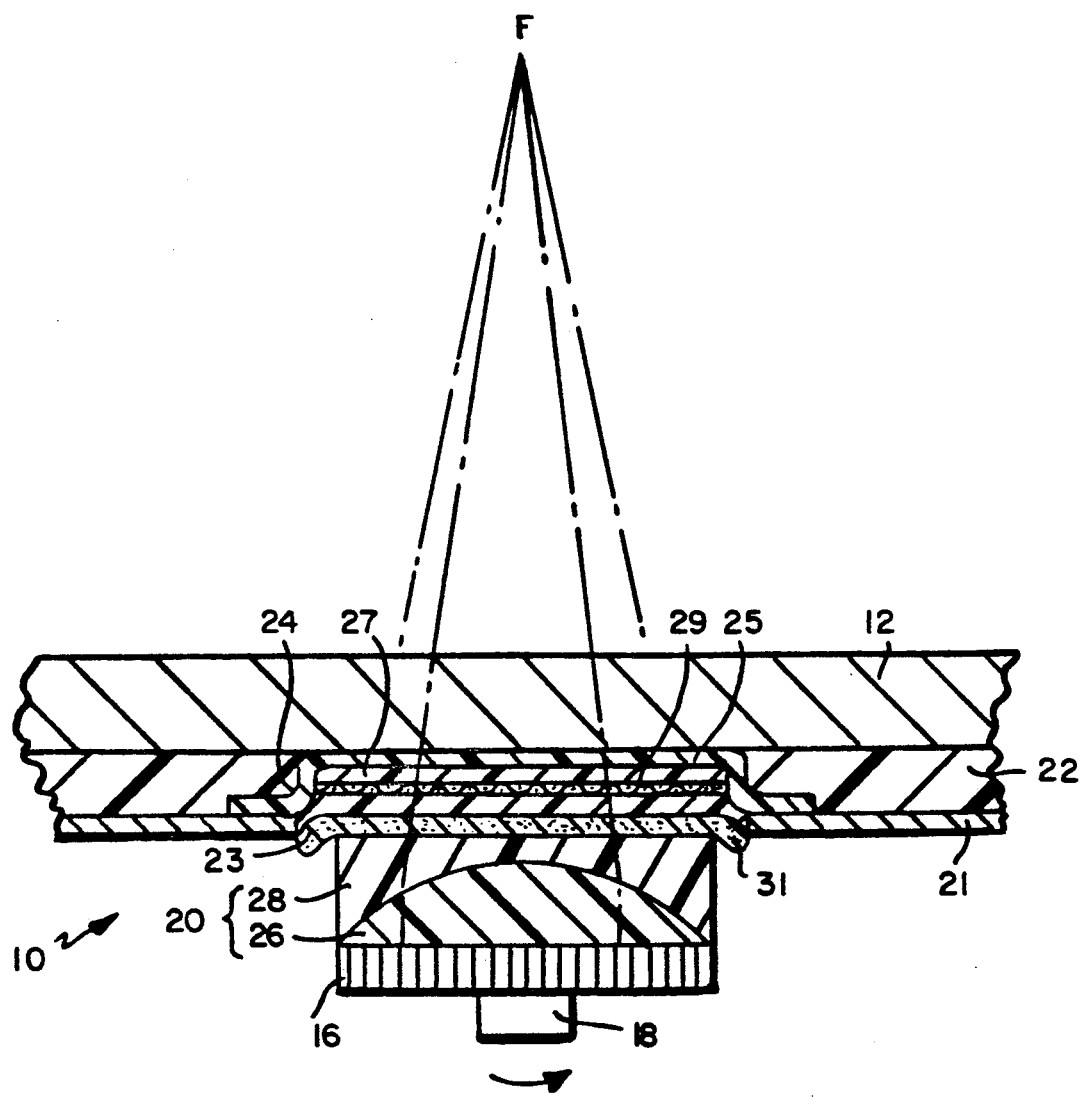

ULTRASOUND PROBE AND LENS ASSEMBLY FOR USE THEREIN

FIELD OF THE INVENTION

This invention relates to ultrasonic transducer systems and more particularly to an ultrasonic transducer probe and to lens assemblies for use therein.

BACKGROUND OF THE INVENTION

Ultrasonic transducers, and in particular phased array ultrasonic transducers, are frequently utilized for a variety of medical and other scanning applications. For such applications, and in particular medical applications, the transducer of the ultrasonic scanner is generally positioned adjacent to a selected outer portion of the body, for example, adjacent to the chest wall to scan the heart. However, superior images can be obtained in at least some applications by positioning the transducer at the end of an endoscope which is suitably positioned in the patient's esophagus. Where this transducer or probe, which is referred to as a transesophageal probe, is utilized for scanning the heart, the procedure is referred to as transesophageal echocardiography (TEE). In order to permit multiple cross-sectional planes of the heart to be scanned, it would be desirable if the transducer array could be rotated.

However, since a probe of this type is inside the body, the probe must be sealed to protect it against attack from body fluids and acids, as well as against sterilant solutions and cleaning solutions either inside or outside the body. This requires the transducer, and any focusing lens thereon, to be enclosed and sealed within a protective housing which does not move as the transducer and lens are rotated. The housing, which is preferably of metal, may be sealed and electrically isolated from the patient by having an epoxy covering molded over it. However, neither the metal housing nor the epoxy covering will transmit ultrasonic signals from the transducer or the echo signal returned theretos. Therefore, it is necessary that an opening be formed in the housing and epoxy covering over the transducer array through which ultrasonic signals may pass.

However, this opening must also be sealed. In order to avoid acoustic distortion from the sealing medium, this seal would typically be a thin plastic film, such as for example a Mylar film, attached to the housing. Such a sealing medium, which is generally flexible, also protects the body from irritation as a result of probe rotation. However, since air has different acoustic properties than the focusing lens and the body being scanned, and thus causes undesired reflection of acoustic waves passed therethrough, it is necessary that either (a) an acoustic medium, typically a fluid, having suitable acoustic characteristics, be provided to transmit the ultrasonic waves; or (b) that the lens be pressed tightly against the flexible sealing medium. With the latter solution, the curved, generally cylindrical, shape of the lens deforms the sealing medium when the array is rotated, distorting the acoustic imaging beam. For the former solution, the acoustic medium is particularly necessary to fill the space between the focusing lens, which is typically curved, and the generally flat sealing film. However, the rotating curved lens causes churning of the acoustic medium and may also cause the outer covering film to distort, disturbing the acoustic waves passing through both the medium and the film. This is particularly true for a cylindrical lens which is preferable for focusing each element of the array, but which causes edge turbulence in the medium.

Further, the thin film which is used to seal the opening in the housing has little structural strength and is, therefore, subject to both distortion which may adversely affect acoustic imaging and to rupture. Therefore, it is generally desired to have a structural backing for this thin film layer. However, the acoustic properties of the backing for the thin film sealing element should not cause undesired distortion of the ultrasonic signals either transmitted or received by the transducer array. It is also desirable that a radio frequency interference (RFI) shield be provided between the body and the array to reduce noise in the array output.

A need, therefore, exists for an improved ultrasonic transducer probe which permits ultrasonic signals to be transmitted from a rotating transducer array through a stationary housing and seal, and in particular for an improved technique for accomplishing this objective in a transesophageal or other invasive probe.

Similar problems may also arise for noninvasive probes where a precise location is required for various imaging planes. In such application, the probe could be placed against the body and the array rotated to obtain different sector scans. Another nonrotational area where similar problems arise is in vascular probe imaging near the surface, or in other similar applications, where a vertical standoff of the probe is required to permit the beam to properly focus or to get adequate beam width for a sector scan. To avoid beam distortion, it is desirable that the offset area between the body and the probe not be filled with air.

SUMMARY OF THE INVENTION

In accordance with the above, this invention provides an ultrasonic transducer probe for medical scanning of a body and, in particular, a lens assembly for use therein. The probe has a housing in which an ultrasonic transducer or transducer array is mounted. An opening is provided in the housing in the area adjacent the transducer. The housing is sealed by a suitable means such as an epoxy coating with there also being an opening in the coating in the area overlying the opening in the housing. A first lens subassembly is mounted to the transducer and a second lens subassembly is mounted to the housing to fill the opening therein. The second lens subassembly includes a means for sealing the opening, for example, a thin plastic film covering the opening which is bonded to the housing in the area thereof around the opening. The lens subassemblies are formed of materials having relative acoustic properties, and having mating surfaces which are shaped, to selectively focus ultrasonic signals from said transducers.

For a preferred embodiment, the first lens subassembly is a compound lens having a first lens section of a first material with first acoustic properties and a second lens section of a second material with second acoustic properties. The first lens section has a first substantially flat surface in contact with the transducer and a second surface opposite the first surface, which surface may have a convex curve. The second lens section has a first surface mating with the second surface of the first lens section and an opposed second flat surface which is substantially parallel to the transducer and to the first surface of the first section. The acoustic properties of the second section are, preferably, substantially the same as those of a body to be scanned, and the relative acoustic properties of the first and second materials and the curves of the mating surfaces are preferably such that the ultrasonic signals from the transducers are selectively focused. The first and second lens sections are preferably formed such that they are adhered together and no air exists at the interface.

Where the transducer is being used to perform transesophageal echocardiography, or for other rotational applications, means are provided for fixing the lens to the transducer and, preferably, for rotating the transducer and lens. Where, as indicated above, the focusing of the ultrasonic signals is performed by the first lens subassembly, the acoustic properties of the second lens subassembly should be substantially the same as those of the body being scanned. In particular, the second lens subassembly preferably includes a thin plastic film covering the openings and bonded to the housing in the area thereof around the openings and a structural backing for the film which is preferably of a material and is shaped relative to the first lens subassembly at the junction thereof so as not to alter the acoustic paths of ultrasonic signals passing therethrough. Where focusing of the ultrasonic signals is not accomplished solely by the first lens subassembly, then the backing for the thin plastic film could also be a lens which cooperates with the first lens subassembly to properly focus the ultrasonic signals. Particularly where the transducer array is being rotated, a thin layer of a low vapor pressure fluid is provided between the first and second lens subassemblies. An RFI screen may also be embedded in the structural backing of the second lens subassembly.

The foregoing and other objects, features and advantages of the invention will be apparent from the following more particular description of a preferred embodiment of the invention as illustrated in the accompanying drawing.

IN THE DRAWINGS

The FIGURE is a cutaway side view of a portion of a transesophageal probe utilizing the lens assembly of this invention.

DETAILED DESCRIPTION

Referring to the FIGURE, a probe 10 is located in the esophagus or other internal body channel 12 of a patient on which, for example, transesophageal echocardiography is being performed. However, while for the preferred embodiment it is assumed that the probe 10 is an invasive transesophageal probe, as previously indicated, this is not a limitation on the invention. The probe has, for example, a standard phased array ultrasonic transducer array 16 formed of piezoelectric material. Transducer array 16 is rotated by being mounted to a mechanism 18 which either directly or indirectly rotates the transducer utilizing a reciprocating motor or other suitable means. The mechanism for rotating the transducer does not form part of the present invention.

A compound lens 20 forms a first lens subassembly. Lens 26 is preferably (but not limited to) cylindrical to permit focusing of each element of the array and is mounted on top of transducer 16 and secured thereto by a suitable glue or other known means. Transducer 16, mechanism 18 and lens 20 are mounted within a housing 21 which is covered by an epoxy seal 22. Additional hardware and circuitry would typically also be contained within housing 21. Since housing 21, which would typically be formed of a metal, and epoxy seal 22 do not pass ultrasonic signals, or do not pass such signals in undistorted form, openings 23 and 24 are provided in the housing and coating, respectively, through which ultrasonic signals may pass.

The openings 23 and 24 are filled and sealed by a second lens subassembly consisting of a thin polyester or other plastic film 25, for example, a Mylar film, with or with a backing layer 27 formed thereto An RFI screen 29 is embedded in backing layer 27. The small space between the first lens subassembly mounted to rotating transducer array 16 and the second lens subassembly which is secured to stationary housing 21 is filled with a thin layer 31 of a low vapor pressure fluid which may for example be an oil, but is preferably a semisolid acoustic grease, for example, a fluorosilicone grease.

Compound lens 20 is in two parts or sections. The first section of lens 20 is convex lens 26 of a first material having selected acoustic properties. Lens section 26 may, for example, be of a silicone rubber such as RTV-560 available from General Electric. The second section of compound lens 20 is a concave section 28 which mates to convex section 26 and is formed of a material having substantially the same acoustic properties as the body being scanned. A suitable material for lens section 28 is a urethane rubber such as RP-6400 available from Ciba Geigy. The two sections of lens 20 are preferably formed together so that they bond to each other without there being an adhesive or other specific bond line therebetween and no air exists at the interface.

The second lens subassembly is preferably formed by bonding the thin polyester film, for example, Mylar, which may, for example, be in the range of ½ mil thick, to the outside of housing 21 in the area of opening 23 with the film covering the opening. The film may then be vacuum formed to expand into and substantially fill openings 23 and 24. RFI screen 29 may then be dropped in the expanded film, being supported, for example, on a shoulder (not shown) in the housing, and the material of backing layer 27 then poured into the expanded film to fill the opening therein as shown in the FIGURE. Layer 27 functions in a lens section and is preferably of a material having substantially the same acoustic characteristics as the body, for example a urethane rubber such as RP-6400 (i.e. the same material as used for lens section 28).

The lower flat surface of lens section 26 is bonded to the upper surface of transducer 16 with a suitable adhesive which is thin enough so as not to refract the ultrasonic signals from the transducer 16. Therefore, ultrasonic waves 30 emitted from transducer 16 are not refracted at the junction between transducer 16 and lens section 26, these signals continuing, as shown in the Figure, in a direction perpendicular to the upper surface of the transducer.

However, the materials of lens sections 26 and 28 and the curve at the junction between these two lens sections are such that acoustic waves at this junction are refracted to converge at a desired focal point F. Since the material of lens section 28 and the material of backing layer or lens 27 are preferably of the same material and, therefore, have the same or substantially the same acoustic properties, which properties are substantially the same as those of the patient s body, and since film layer 25 and acoustic grease layer 31 are extremely thin (i.e., less than 1/10 of a wavelength), and are therefore substantially transparent to acoustic waves, the acoustic beams are not refracted or bent at the junctions between lens section 28 and grease 31, between grease 31 and layer 27, between layer 27 and film 25 or between film 25 and internal body channel 12. In this regard, it is important that the outer surface of lens section 28 be flat and substantially parallel to the upper surface of transducer 16 (and thus to the lower surface of lens section 26), and that this surface substantially mate and be in contact with a flat, parallel lower surface of backing layer 27 so that no air is between these two surfaces. Air between these two surfaces would cause undesired reflection or refractions of the acoustic waves. Acoustic grease 31 lubricates the contacting surfaces of lens section 28 and lens or backing 27 so that the rotating lens section may move relative to the stationary housing and second lens subassembly affixed thereto without rippling the film layer 25 or causing damage thereto, and also serves to seal and keep air out of the junction between lens section 27 and 28.

A simple lens assembly is thus provided which permits a transesophageal probe or other similar device to be sealed in a suitable housing, and for the housing and its seals to remain stationary while the transducer and its focusing lens are rotated to permit multiple planes to be scanned, without causing undesired reflection of the acoustic waves as a result of air in the acoustic path, or bending as a result of ripples in an acoustic medium, or rippling of a sealing film.

While the two lens sections are formed together for the preferred embodiment, they may also be secured together by other suitable means such as an acoustic adhesive having suitable properties. With spherical or flat lenses, it is also possible to fix one lens section to the rotated transducer 16 and to use lens or backing layer 27 as the other lens section which is fixed to the housing. For this configuration, the shape of lens 27 might need to be modified to provide proper focusing of the ultrasonic signals. A suitable lubricating agent would be utilized between the relatively rotating lenses. A replaceable lubricating agent, such as an acoustic coupling gel, may be used in place of the acoustic grease 31 for noninvasive applications.

Further, while particular lens shapes and materials have been described above, it is apparent that both the shapes of lens sections 26, 27 and 28 and the materials utilized therefore may vary with specific application. Thus, for a particular application and lens section material, the convex and concave lens sections may be reversed or the sections may be flat. What is required is that the sections mate. Further, lens sections 26 and 28 may only partially focus the ultrasonic signals and lens 27 may be utilized to complete the focusing operation.

Therefore, while the invention has been particularly shown and described with reference to a preferred embodiment, the foregoing and other changes in form and detail may be made therein by one skilled in the art without departing from the spirit and scope of the invention.

What is claimed is:

1. A lens assembly for use with an ultrasonic transducer array mounted in a housing, there being an opening in the housing in the portion thereof adjacent the array, the array being used for medical scanning of a body part, the lens assembly comprising:
a first lens subassembly comprising compounded lenses mounted to the array; and
a second lens subassembly mounted to the housing to fill said opening therein, and including means for sealing said opening;
said lens subassemblies being combined to form said lens assembly and comprising materials having related acoustic properties, and having surface shapes which selectively focus ultrasonic signals from said transducer array.

2. A lens assembly as claimed in claim 1 wherein said first lens subassembly comprises a first lens section of a first material having first acoustic properties, said first lens section having a first substantially flat surface in contact with said transducer array, and a second surface opposite said first surface; and
a second lens section of a second material having second acoustic properties, said second lens section having a first surface mating with the second surface of said first lens section and an opposed flat second surface which is substantially parallel to said transducer array and to the first surface of said first section.

3. A lens assembly as claimed in claim 2 wherein the acoustic properties of said second material are substantially the same as those of a body part being scanned.

4. A lens assembly as claimed in claim 2 wherein the relative acoustic properties of said first and second materials and the curves of the mating surfaces of the first and second sections are such that ultrasonic signals from said transducer array are selectively focused.

5. A lens assembly as claimed in claim 4 wherein said first material is a silicone rubber and said second material is a urethane rubber.

6. A lens assembly as claimed in claim 4 wherein the second surface of said first lens section is a convex curved surface and wherein the first surface of said second lens section is a mating concave surface.

7. A lens assembly as claimed in claim 2 wherein said first and second lens sections are formed together.

8. A lens assembly as claimed in claim 1 wherein focusing of said ultrasonic signals is performed by said first lens subassembly; and
wherein the acoustic properties of the second lens subassembly are substantially the same as those of a body part being scanned.

9. A lens assembly as claimed in claim 8 wherein said second lens subassembly includes a thin plastic film covering said opening and bonded to said housing in an area thereof around said opening, and a structural backing for said film which is of a material and is shaped relative to said first lens subassembly at a junction between the backing nd said first lens subassembly so as not to alter the acoustic paths of ultrasonic signals passing therethrough.

10. A lens assembly as claimed in claim 9 wherein the mating surfaces of said first and second lens subassemblies are the flat second surfaces of said second lens section and a mating flat surface of said structural backing.

11. A lens assembly as claimed in claim 9 including a thin layer of a low vapor pressure fluid between said first and second lens subassemblies.

12. A lens assembly as claimed in claim 1 wherein said second lens subassembly includes a thin plastic film covering said opening and bonded to said housing in an area thereof around said opening, and a structural backing for said film.

13. A lens assembly as claimed in claim 12 wherein there is relative movement between said first and second lens assemblies; and including a thin layer of a low vapor pressure fluid between said first and second lens subassemblies.

14. A lens assembly as claimed in claim 12 including an RFI screen embedded in said structural backing.

15. A lens assembly as claimed in claim 12 wherein said plastic film has a formed shape to fill said opening and wherein said backing is of urethane and fills the formed plastic film shape.

16. An ultrasonic probe used for medical scanning of a body comprising:
  an ultrasonic transducer having a side from which ultrasonic waves are preferentially emitted;
  a housing in which said transducer is mounted, said housing having an opening adjacent said transducer side;
  means for sealing said housing, said means for sealing having an opening which overlies the housing opening;
  a first lens subassembly comprising compound lenses mounted to the transducer side; and
  a second lens subassembly mounted to the housing to fill said opening therein, and including means for sealing said opening;
  said lens subassemblies comprising materials having related acoustic properties, and having surface shapes, to selectively focus ultrasonic signals from said transducer.

17. A probe as claimed in claim 16 wherein said transducer is rotatable, and including a thin layer of a low vapor pressure fluid between said first and second lens assemblies.

18. A probe as claimed in claim 17 wherein said mating surfaces are flat and substantially parallel to the side of the transducer.

19. A probe as claimed in claim 16 wherein said means for sealing the housing is an epoxy layer over the housing.

20. A probe as claimed in claim 19 wherein said second lens subassembly includes a thin plastic film covering said opening and sealed to said housing in an area thereof around said opening, and a structural backing for said film.

* * * * *